United States Patent [19]

Van Solingen

[11] Patent Number: 5,856,165

[45] Date of Patent: Jan. 5, 1999

[54] ALKALINE CELLULASE AND METHOD OF PRODUCING SAME

[75] Inventor: Pieter Van Solingen, Naaldwijk, Netherlands

[73] Assignee: Genencor International, Rochester, N.Y.

[21] Appl. No.: 727,548

[22] PCT Filed: Apr. 26, 1996

[86] PCT No.: PCT/US96/05652

§ 371 Date: Jun. 4, 1997

§ 102(e) Date: Jun. 4, 1997

[87] PCT Pub. No.: WO96/34108

PCT Pub. Date: Oct. 31, 1996

[30] Foreign Application Priority Data

Apr. 28, 1995 [EP] European Pat. Off. ............... 95201115

[51] Int. Cl.⁶ ..................................................... C12N 9/42
[52] U.S. Cl. ........................ 435/209; 435/69.1; 530/350; 8/115.56

[58] Field of Search ................................... 435/209, 69.1; 530/350; 8/115.56

[56] References Cited

U.S. PATENT DOCUMENTS 5,741,693  4/1998  Outtrup et al. ..................... 435/221

OTHER PUBLICATIONS

Kenkyusho (1987) GenBank Accession No. P81843.
Park et al. (1993) Protein Engineering 6/8, pp. 921–926.

Primary Examiner—Robert A. Wax
Assistant Examiner—Enrique D. Longton
Attorney, Agent, or Firm—Christopher L. Stone

[57] ABSTRACT

The present invention provides a novel cellulase composition obtainable from Bacillus sp. CBS 670.93. A preferred cellulase has a calculated molecular weight of approximately 50 kD, a calculated isoelectric point of about 4 and a pH optimum on CMC of about 6–10 at 40° C. and about 7 at 60° C.

5 Claims, 3 Drawing Sheets

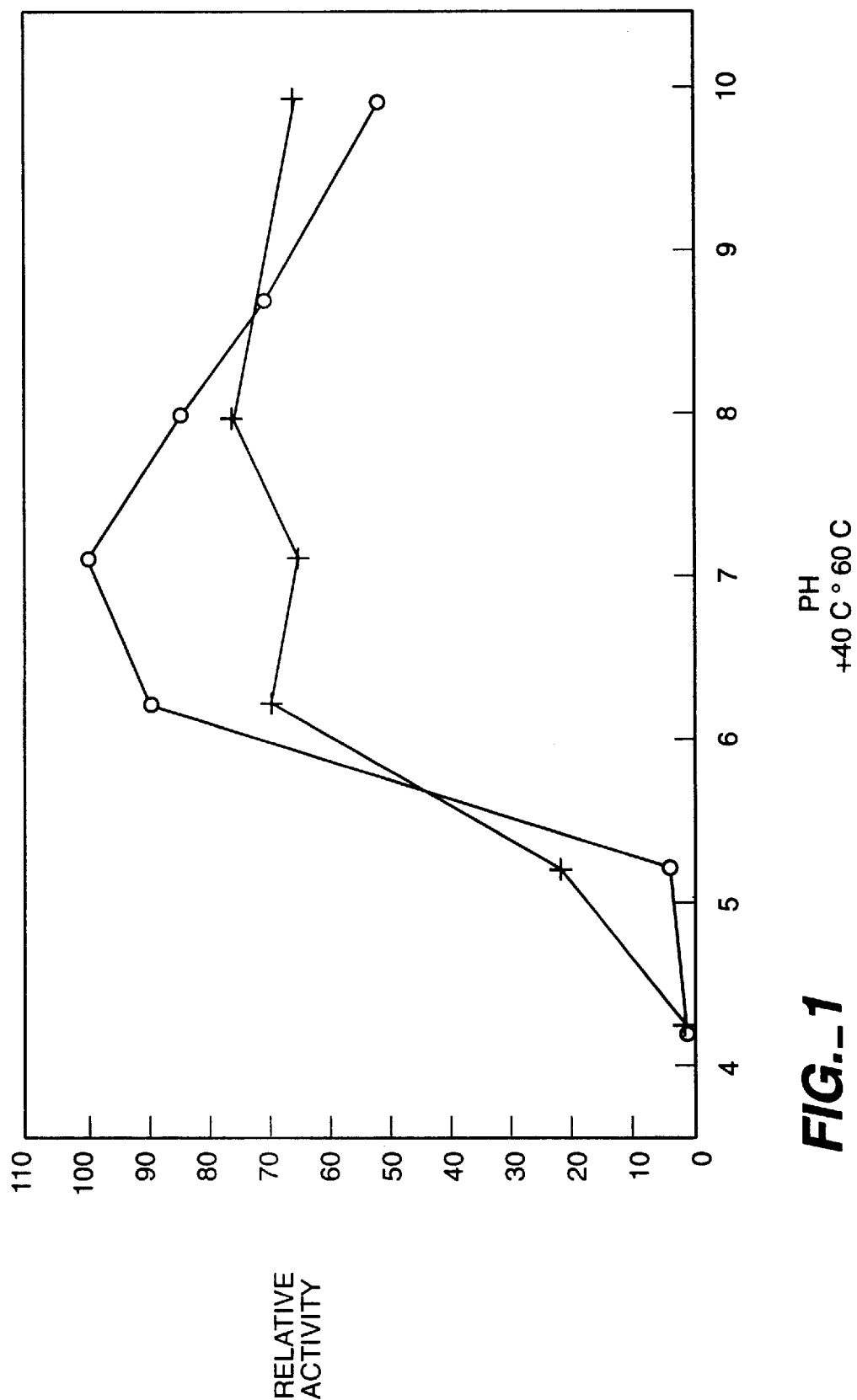
FIG._1

```
-121  GAATTCCGTTACATATTTTGCAAAAAGAGGGTGGTGGCGCTACATATACACCTTAAAAAG

-60  TGCAGACTAAAACGATTTCGTTTCAGTATGAAAAGCTAAACCATTACCAAGGAGGAAATT

1  ATGAAAAAGATAACTACTATTTTTGCCGTATTGCTCATGACATTGGCGTTGTTCAGTATA
      MetLysLysIleThrThrIlePheAlaValLeuLeuMetThrLeuAlaLeuPheSerIle

61  GGAAACACGACAGCGGCTGATGATTATTCAGTTGTAGAGGAACATGGGCAACTAAGTATT
      GlyAsnThrThrAlaAlaAspAspTyrSerValValGluGluHisGlyGlnLeuSerIle

121  AGTAACGGTGAATTAGTCAATGAACGAGGCGAACAAGTTCAGTTAAAAGGGATGAGTTCC
      SerAsnGlyGluLeuValAsnGluArgGlyGluGlnValGlnLeuLysGlyMetSerSer

181  CATGGTTTGCAATGGTACGGTCAATTTGTAAACTATGAAAGCATGAAATGGCTAAGAGAT
      HisGlyLeuGlnTrpTyrGlyGlnPheValAsnTyrGluSerMetLysTrpLeuArgAsp

241  GATTGGGGAATAACTGTATTCCGAGCAGCAATGTATACCTCTTCAGGAGGATATATTGAC
      AspTrpGlyIleThrValPheArgAlaAlaMetTyrThrSerSerGlyGlyTyrIleAsp

301  GATCCATCAGTAAAGGAAAAAGTAAAAGAGACTGTTGAGGCTGCGATAGACCTTGGCATA
      AspProSerValLysGluLysValLysGluThrValGluAlaAlaIleAspLeuGlyIle

361  TATGTGATCATTGATTGGCATATCCTTTCAGACAATGACCCGAATATATATAAAGAAGAA
      TyrValIleIleAspTrpHisIleLeuSerAspAsnAspProAsnIleTyrLysGluGlu

421  GCGAAGGATTTCTTTGATGAAATGTCAGAGTTGTATGGAGACTATCCGAATGTGATATAC
      AlaLysAspPhePheAspGluMetSerGluLeuTyrGlyAspTyrProAsnValIleTyr

481  GAAATTGCAAATGAACCGAATGGTAGTGATGTTACGTGGGACAATCAAATAAAACCGTAT
      GluIleAlaAsnGluProAsnGlySerAspValThrTrpAspAsnGlnIleLysProTyr

541  GCAGAAGAAGTGATTCCGGTTATTCGTGACAATGACCCTAATAACATTGTTATTGTAGGT
      AlaGluGluValIleProValIleArgAspAsnAspProAsnAsnIleValIleValGly

601  ACAGGTACATGGAGTCAGGATGTCCATCATGCAGCCGATAATCAGCTTGCAGATCCTAAC
      ThrGlyThrTrpSerGlnAspValHisHisAlaAlaAspAsnGlnLeuAlaAspProAsn

661  GTCATGTATGCATTTCATTTTTATGCAGGAACACATGGACAAAATTTACGAGACCAAGTA
      ValMetTyrAlaPheHisPheTyrAlaGlyThrHisGlyGlnAsnLeuArgAspGlnVal

721  GATTATGCATTAGATCAAGGAGCAGCGATATTTGTTAGTGAATGGGGGACAAGTGCAGCT
      AspTyrAlaLeuAspGlnGlyAlaAlaIlePheValSerGluTrpGlyThrSerAlaAla

781  ACAGGTGATGGTGGTGTGTTTTTAGATGAAGCACAAGTGTGGATTGACTTTATGGATGAA
      ThrGlyAspGlyGlyValPheLeuAspGluAlaGlnValTrpIleAspPheMetAspGlu

841  AGAAATTTAAGCTGGGCCAACTGGTCTCTAACGCATAAGGATGAGTCATCTGCAGCGTTA
      ArgAsnLeuSerTrpAlaAsnTrpSerLeuThrHisLysAspGluSerSerAlaAlaLeu

901  ATGCCAGGTGCAAATCCAACTGGTGGTTGGACAGAGGCTGAACTATCTCCATCTGGTACA
      MetProGlyAlaAsnProThrGlyGlyTrpThrGluAlaGluLeuSerProSerGlyThr
```

FIG._2A

```
 961  TTTGTGAGGGAAAAAATAAGAGAATCAGCATCTATTCCGCCAAGCGATCCAACACCGCCA
      PheValArgGluLysIleArgGluSerAlaSerIleProProSerAspProThrProPro

1021  TCTGATCCAGGAGAACCGGATCCAGGAGAACCGGATCCAACGCCCCCAAGTGATCCAGGA
      SerAspProGlyGluProAspProGlyGluProAspProThrProProSerAspProGly

1081  GAGTATCCAGCATGGGATTCAAATCAAATTTACACAAATGAAATTGTGTATCATAACGGT
      GluTyrProAlaTrpAspSerAsnGlnIleTyrThrAsnGluIleValTyrHisAsnGly

1141  CAGTTATGGCAAGCGAAATGGTGGACACAAAATCAAGAGCCAGGTGACCCATACGGTCCG
      GlnLeuTrpGlnAlaLysTrpTrpThrGlnAsnGlnGluProGlyAspProTyrGlyPro

1201  TGGGAACCACTCAAATCTGACCCAGATTCAGGAGAACCGGATCCAACGCCCCCAAGTGAT
      TrpGluProLeuLysSerAspProAspSerGlyGluProAspProThrProProSerAsp

1261  CCAGGAGAGTATCCAGCATGGGATTCAAATCAAATTTACACAAATGAAATTGTGTACCAT
      ProGlyGluTyrProAlaTrpAspSerAsnGlnIleTyrThrAsnGluIleValTyrHis

1321  AACGGCCAGCTATGGCAAGCAAAATGGTGGACACAAAATCAAGAGCCAGGTGACCCATAT
      AsnGlyGlnLeuTrpGlnAlaLysTrpTrpThrGlnAsnGlnGluProGlyAsnProTyr

1381  GGTCCGTGGGAACCACTCAATTAAACTATATAATTGATAAAAATTTACTAATGAGATAGT
      GlyProTrpGluProLeuAsnEnd

1441  GAGAATCCCAAGAGTCTAAATTTGAAGATTGGCATTCTCATTTTACAATTAATTTAATCC

1501  ATTGAAAATATTTAAAAACGAATTTTATAATATCCAAGGTACCATACTTAATTGGCGGTA

1561  CTTTTTTCTGTCCTTATAGCTGCCCATCCCCCCGAAAAAGCGGTCGAAAACTGGTGCATT

1621  TTTCAGCATTATCTTGTAAATATCAAAACATAAGAAAAAGCCTTGAAACATTGATATGAC

1681  AACGTTTCTAAGGCTTTTCTGCATTTCTTATTCAGTGTATGCCAATTAACGAGAGTACCA

1741  CTCAACGATAAGTTGTTCGTTAATTTCAGCTGGAAGCTCAGAACGCTCAGGTAAACGAGT

1801  GAACGTACCTTCAAGCTT
```

FIG._2B

ALKALINE CELLULASE AND METHOD OF PRODUCING SAME

BACKGROUND OF THE INVENTION

A. Technical field

The present invention relates to novel cellulase compositions. The invention further relates to novel cellulase compositions, preferably derived from Bacillus sp. The present invention further relates to the use of the novel cellulase in compositions recognized in the art as advantageously having cellulase added thereto, including, as an additive in a detergent composition, in the treatment of cellulose containing fabrics, in the treatment of pulp and paper and in the treatment of starch for the production of high fructose corn-syrup or ethanol.

B. State of the Art

Cellulases are enzymes which are capable of the hydrolysis of the 1,4 β-D-glucosidic linkages in celluloses. Cellulolytic enzymes have been traditionally divided into three major classes: endoglucanases, exoglucanases or cellobiohydrolases and β-glucosidases (Knowles, J. et al. (1987), TIBTECH 5, 255–261); and are known to be produced by a large number of bacteria, yeasts and fungi.

Primary among the applications that have been developed for the use of cellulolytic enzymes are those involving degrading (wood)cellulose pulp into sugars for (bio)ethanol production, textile treatments like 'stone washing' and 'biopolishing', and in detergent compositions. Thus, cellulases are known to be useful in detergent compositions for removing dirt, i.e., cleaning. For example, Great Britain Application Nos. 2,075,028, 2,095,275 and 2,094,826 illustrate improved cleaning performance when detergents incorporate cellulase. Additionally, Great Britain Application No. 1,358,599 illustrates the use of cellulase in detergents to reduce the harshness of cotton containing fabrics.

Another useful feature of cellulases in the treatment of textiles is their ability to recondition used fabrics by making their colors more vibrant. For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Despite knowledge in the art related to many cellulase compositions having some or all of the above properties, there is a continued need for new cellulases having a varying spectrum of characteristics which are useful in, for example, treating textiles, as a component of detergent compositions, in the treatment of pulp and paper, and in the conversion of biomass. Applicants have discovered certain cellulases which have such a complement of characteristics and which are useful in such known applications of cellulase.

SUMMARY OF THE INVENTION

It is an object of the present invention to provide a novel cellulase having beneficial properties for use in detergents, treating textiles and pulp and paper manufacturing.

According to the present invention, a cellulase is obtainable from or derived from Bacillus sp. CBS 670.93, or a derivative of said cellulase. CBS 670.93 is deposited at the Centraalbureau voor Schimmelcultures (CBS), Baam, Netherlands under accession number CBS 670.93, on Dec. 23, 1993 ("CBS 670.93"). Preferably, the novel cellulase comprises an amino acid sequence according to FIG. 2 (SEQ ID NO:2), or a derivative thereof having greater than 89% sequence identity, preferably at least 95% sequence identity thereto. The present invention is also directed to a novel cellulase comprising an amino acid sequence according to FIG. 2 (SEQ ID NO:2), or a derivative thereof having greater than 92.5% sequence similarity, preferably greater than 97% sequence similarity thereto.

According to another embodiment, a composition is provided comprising DNA which encodes an amino acid sequence according to FIGS. 2 (SEQ ID NO:2), or a derivative thereof having greater than 89% sequence identity, preferably 95% sequence identity thereto. Alternatively, a composition is provided comprising DNA which encodes an amino acid sequence according to FIGS. 2 (SEQ ID NO:2), or a derivative thereof having greater than 92.5% sequence similarity, preferably greater than 97% sequence similarity thereto.

According to yet another embodiment of the invention, a method of transforming a suitable microorganism with DNA encoding an amino acid sequence according to the invention is provided. Additionally, a microorganism transformed with DNA according to the invention is provided.

In an especially preferred embodiment of the present invention, the cellulase is a cellulase derived from Bacillus sp. CBS 670.93 having a calculated molecular weight of approximately 50 kD. The approximately 50 kD cellulase has a calculated isoelectric point of about 4 and a pH optimum on CMC of about 6–10 at 40° C. and about 7 at 60° C.

BRIEF DESCRIPTION OF THE FIGURES

FIG. 1 shows the pH profile activity of an approximately 50 kD cellulase derived from CBS 670.93 at 40° C. and 60° C.

FIGS. 2a and 2b show the DNA sequence (SEQ ID. NO. 1) and deduced amino acid sequence (SEQ ID. NO. 2) for the 50 kD cellulase derived from CBS 670.93 with the leader peptide sequence underlined, which upon secretion is cleaved to yield the mature enzyme.

DETAILED DESCRIPTION OF THE INVENTION

"Derivative" is intended to indicate a protein which is derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme according to the present invention) and which peptides retain a characteristic enzyme nature of the precursor enzyme but which have altered properties in some specific aspect. For example, an altered cellulase may have an increased pH optimum or increased temperature resistance but will retain its characteristic cellulolytic activity.

Derivatives also includes chemical modifications of amino acid residues within the enzyme molecule.

A cellulase is "obtainable from" Bacillus 670.93 if such cellulase has an amino acid sequence which corresponds to the amino acid sequence of a cellulase which may be obtained from that organism. Thus cellulase with an identical amino acid sequence to the 50 kD cellulase of the invention derived from a different Bacillus would be "obtainable from" Bacillus 670.93.

"Host cell" means a cell which has the capacity to act as a host and expression vehicle for a recombinant DNA vector according to the present invention. In a preferred embodiment according to the present invention, "host cell" means the cells of Bacillus.

"DNA construct" or "DNA vector" means a nucleotide sequence which comprises one or more DNA fragments encoding any of the novel cellulases or cellulase derivatives described above.

In a preferred embodiment, the cellulase is obtainable from the Centraal Bureau voor Schimmelcultures, Baam, the Netherlands through microorganism deposition number CBS 670.93 (described in application PCT/EP94/04312), deposited under the Budapest Convention on Dec. 23, 1993. As used herein, the deposited species will be referred to as CBS 670.93. In a more preferred embodiment, the cellulase of the invention is an approximately 50 kD cellulase (calculated on the basis of amino acid sequence of the mature protein) derived from CBS 670.93 (referred to herein as the "50 kD Cellulase"). The approximately 50 kD cellulase has a calculated pi for the mature protein of about 4 and a pH optimum on CMC of about 6–10 at 40° C. and about 7 at 60° C.

The gene encoding the amino acid sequence of the approximately 50 kD cellulase was analyzed by comparison with the accessible sequence data in various libraries (GenBank, Swiss-Prot, EMBL and PIR) using the of CAOS/CAMM Center, University of Nijmegen, Holland. A search of databases for a comparison of the cellulase encoded by the DNA sequence of the present invention with cellulases encoded by published or known cellulase gene sequences revealed that the greatest amount of amino acid identity was found in the cellulase CelA of Bacillus sp. N-4 (Fukumori et al., J. Bacter., vol. 168, pp. 479–485 (1986)).

The approximately 50 kD cellulase was shown to be 89% identical in sequence and 92.5% similar in sequence using the TFastA program as described by Pearson & Lipman, Proc. Nat. Acad. Sci., vol. 85, pp. 2444–2448 (1988) to the closest published cellulase sequence. The TFastA Data Searching Program is commercially available in the Sequence Analysis Software Package Version 6.0 (Genetic Computer Group, Univ. Wisconsin Biotechnology Center, Madison, Wis. 53705). Thus, the present invention encompasses a cellulase which has an amino acid sequence according to that in FIG. 2 (SEQ ID NO:2) or a derivative thereof having greater than 89% sequence identity, preferably greater than 95% sequence identity thereto. The present invention further encompasses a cellulase which has an amino acid sequence having greater than 92.5% sequence similarity, preferably greater than 97% sequence similarity to the amino acid sequence according to FIG. 2 (SEQ ID NO:2).

The present invention also discloses a process for the production of the cellulase. In one embodiment, the cellulase may be produced by cultivating a suitable organism, e.g., Bacillus sp. CBS 670.93, under conditions so as to produce the cellulase. Preferably, such conditions include those generally suggested for the cultivation of Bacillus to maximize cellulase production and include the use of a cellulose derived substrate as an energy source in combination with necessary salts, ions and other well known ingredients. Generally, the medium used to cultivate the cells may be any conventional medium suitable for growing bacteria. The cells may be cultivated under aerobic conditions in a nutrient medium containing assimilable carbon and nitrogen together with other essential nutrients. Suitable carbon sources are carbohydrates such as sucrose, glucose and starch, or carbohydrate containing materials such as cereal grain, malt, rice and sorghum. The carbohydrate concentration incorporated in the medium may vary Widely, e.g., up to 25% and down to 1–5%, but usually 8–10% will be suitable, the percentages being calculated as equivalents of glucose. The nitrogen source in the nutrient medium may be of inorganic and/or organic nature. Suitable inorganic nitrogen sources are nitrates and ammonium salts. Among the organic nitrogen sources used regularly in fermentation processes involving the cultivation of bacteria are soybean meal, cotton seed meal, peanut meal, casein, corn, corn steep liquor, yeast extract, urea and albumin. In addition, the nutrient medium should also contain standard trace substances.

The cellulase may be recovered from the medium by conventional procedures including separating the cells from the medium by centrifugation or filtration, if necessary after disruption of the cells, precipitating the proteinaceous components of the supernatant or filtrate by means of a salt, e.g., ammonium sulfate, followed by purification by a variety of chromatographic procedures, e.g., ion exchange chromatography, affinity chromatography or similar art recognized procedures. For the production of the alkaline cellulase according to the invention, it is preferred to cultivate under alkaline conditions using media containing a cellulose based energy source.

Preferably, the cellulase according to the present invention is produced utilizing genetic engineering techniques by transforming a suitable host cell with a gene encoding the cellulase and expressing under conditions appropriate for host cell growth and cellulase expression. As a first step, the chromosomal DNA may be obtained from the donor bacterial strain by the method of Saito and Miura (Saito & Miura, Biochim. Biophys. Acta., vol. 72, pp. 619 (1963)) or by a similar method. Restriction enzyme cleavage of the chromosomal DNA thus obtained gives DNA fragments containing the alkaline cellulase gene. For this purpose, any restriction enzyme may be used provided that it does not cleave the region of said gene. In the alternative, a restriction enzyme may be used which cleaves the gene, using however, a reduced enzyme concentration or incubation time to permit only partial digestion. A preferred restriction endonuclease is Sau3A. From the resulting digestion mixture, suitable fragments (2–6 kb) can be isolated and used to transform a suitable host cell with a DNA construct, e.g., with a DNA construct including the approximately 1.9 kb DNA fragment encoding the 50 kD cellulase according to the invention which has been ligated to a suitable vector sequence. The ligation mixture is then transformed into a suitable host.

The gene encoding the cellulase of the present invention can be cloned using λ-phage (expression) vectors and *E. coli* host cells. (Alternatively PCR cloning using consensus primers designed on conserved domains may be used). Applicants have discovered that transformation of the gene encoding the cellulase of the present invention and expression in *E. coli* results in an active protein. After a first cloning step in *E. coli*, a cellulase gene according to the present invention can be transferred to a more preferred industrial expression host such as Bacillus or Streptomyces species, a filamentous fungus such as Aspergillus or Trichoderma, or a yeast such as Saccharomyces. High level expression and secretion obtainable in these host organisms allows accumulation of the cellulase in the fermentation medium from which it can subsequently be recovered.

Preferably, the expression host cell comprises a Bacillus sp., more preferably *Bacillus licheniformis* or *Bacillus subtilis*. In an especially preferred embodiment, the transformation host is deleted for protease genes to ensure that the product cellulase is not subject to proteolysis in the fermentation broth or concentrates thereof. A preferred general transformation and expression protocol for protease deleted Bacillus strains is provided in Ferrari et al., U.S. Pat. No. 5,264,366, incorporated herein by reference. Also preferably, the fermentation of the transformed Bacillus host is conducted at a pH of about 6.9. Transformation and expression in Aspergillus is described in, for example, Berka et al., U.S. Pat. No. 5,364,770, incorporated herein by reference. A preferred promoter when the transformation host cell is Bacillus is the aprE promoter.

The instant approximately 50 kD cellulase derived from CBS 670.93 has been shown to be useful in buffer systems comprising glycine, ammonium acetate, borax and/or tris. This cellulase has also been found to be activated on CMC by the presence of magnesium and inhibited by the presence of calcium. A proportion of calcium to magnesium of about 750 ppm:250 ppm has also been found to result in an activity benefit.

According to the present invention, the cellulase compositions described above may be employed in detergent compositions according to art-recognized methods of utilizing cellulases in detergents. The excellent activity of the instant cellulase at alkaline pH should result in the present cellulase being especially useful in high pH detergents.

The invention will be explained in more detail in the following examples which are provided for illustrative purposes and should not to be construed as limitative of the invention.

EXAMPLE 1

Screening And Isolation of Cellulase From Alkaline Soil And Water Samples

Two methods were applied for the isolation of cellulase-producing microorganisms from alkaline soil and water samples. In one method, the soil and water samples were suspended in 0.85% saline solution and directly used in the carboxymethyl cellulose (CMC)-agar diffusion assay for detection of cellulase producing colonies. In a second method, the soil and water samples were enriched for cellulase containing strains by incubation in a cellulose containing liquid minimal medium or GAM-medium for 1 to 3 days at 40° C. Cultures that showed bacterial growth were analyzed for cellulase activity using the CMC-agar diffusion assay for detection of cellulase producing colonies. The CMC-agar diffusion assay and enrichment procedure utilized a minimal medium preparation at a pH of about 9.7 comprising 1% $KNO_3$, 0.1% yeast extract (Difco), 0.1% $KH_2PO_4$, 0.02% $MgSO_4.7H_2O$, 1% $Na_2CO_3$, 4% NaCl and 0.25% CMC (Sigma C-4888). For solidification 1.5% agar was added.

One of two procedures was used for the CMC-agar diffusion assay depending on whether colonies or liquid fractions were tested. For testing colonies, cell suspensions in 0.85% saline solution were plated on CMC-containing minimal medium. After incubation for 1 to 3 days at 40° C., the plates were replica plated and the parent plate was flooded with 0.1% Congo Red for 15 minutes. The plates were destained with 1 M NaCl for 30 minutes. The strains that showed a clearing zone around the colony were isolated as potential cellulases producing microorganisms. Liquid fractions were assayed by pipetting 40 μl aliquots of enzyme solution or fermentation broth into wells punched out from a layer of 5 mm of minimal medium in a petri dish. After incubation for 16 hours at 40° C. cellulase activity was detected by Congo Red/NaCl treatment. The diameter of the clearing zone is a measure for the CMCase activity.

Strains which showed clearing zones using either of the two screening methods were selected for growing up and isolation of cellulase. The colonies were fermented in 25 milliliter GAM-medium in 100 milliliter shake flasks in an Incubator Shaker (New Brunswick Scientific, Edison, N.J., USA), at 250 r.p.m. at 40° C. for 72 hours. CMCase activity was determined in the culture broth at pH 9 and 40° C. to verify the presence of cellulase in the fermentation broth. The complex medium (GAM) used for enzyme production consisted of Peptone (Difco) 0.5%, Yeast extract (Difco) 0.5%, Glucose. $H_2O$ 1%, $KH_2PO_4$ 0.1%, $MgSO_4.7H_2O$ 0.02%, $Na_2CO_3$ 1%, NaCl 4%. The pH was adjusted to 9.5 with 4 M HCl after which 1% CMC was added.

Utilizing the method described above, a cellulase producing microorganism was isolated which was further characterized as small straight rods, occurring occaisonally in pairs and being motile. The terminal to sub-terminal spores were ellipsoidal with a clear swelling of the sporangium. Colonies on GAM-agar appeared as a creamy white, dull (i.e., not shiny) having an irregular surface with a filamentous margin. Based on 16S rRNA sequence analysis, the microorganism was classified as species of the genus Bacillus. The organism is referred to herein as CBS 670.93 and is deposited in the Centraal Bureau voor Schimmelcultures, Baam, The Netherlands under that accession number.

EXAMPLE 2

Isolation of DNA, Transformation and Expression of Cellulase

The alkaliphilic Bacilli strain CBS 670.93 was chosen as a donor strain for expression cloning in *E. coli*. Chromosomal DNA was isolated according to the method described by Saito & Miura, Biochim. Biophys. Acta., vol. 72, pp. 619–629 (1963).

The isolated chromosomal DNA is partially digested by the restriction enzyme Sau3A using serial diluted enzyme solutions, for one hour at 37° C. using React Buffers (Gibco BRL Life Technologies, Gaithersburg, Md., USA) under conditions recommended by the supplier. The digested DNA is fractionated by agarose gel electrophoresis and suitable fractions (2–6 kb) are isolated from the gel using QlAquick Gel Extraction Kit according to the protocol described by the supplier (QlAGEN Inc., Chatsworth, Calif., USA).

The Sau3A fragments of the chromosomal DNA are used to construct genomic gene libraries in a BamH1, digested ClAP treated ZAP Express vector according to the protocol described by the supplier (Stratagene Cloning Systems, La Jolla, Calif., USA). pBK-CMV phagmids, containing the cloned DNA inserts, were excised from the ZAP Express™ vector and transformed into *E. coli* strain XLOLR.

Recombinant clones are screened by agar diffusion as described by Wood et al., Meth. Enzym., vol.160, pp. 59–74 (1988). Strains that showed clearing zones around the colony are isolated. The CMCase activity of the isolated recombinants is determined after fermentation for 48 hours in 4*YEP-medium consisting of Yeast Extract (Difco) 4%, peptone (Difco) 8%, lactose 0.2%, ampicillin 100 μg/ml. The recombinant protein is purified (Example 3) and the amino acid sequence is determined (SEQ ID: NO 2).

Plasmid DNA of the cellulase producing recombinant is isolated using a QlAprep Plasmid Kit according to the protocol described by the supplier (QlAGEN Inc.). The plasmid contained an approximately 1.9 kb insert of chromosomal DNA. The nucleotide sequence of a fragment of 1933 bp is determined using a set of degenerated oligonucleotides derived from the N-terminal amino acid sequence as a primer to locate the gene on the 1.9 kb insert. The 1933 bp fragment contains an open reading frame of 1422 bp from which a protein of 467 amino acids can be deduced including a 26 amino acid leader sequence. The nucleotide sequence of the gene (SEQ. ID. NO:1) coding for said cellulase and the deduced amino acid sequence (SEQ ID NO:2) of the isolated single cellulase may then be determined and is illustrated in FIG. 2.

EXAMPLE 3

Purification of Cellulase

The cellulase producing clones from Example 2 were grown on a complex medium (4*YEP) consisting of Yeast Extract (Difco) 4%, Peptone (Difco) 8%, lactose 0.2%, 100 μg/ml ampicillin). The fermentation broth was separated from the culture liquid by centrifugation (8000 rpm). The cellulase in the supernatant was precipitated with ammonium sulphate (65% saturation). The precipitate was dissolved in 25 mM phosphate buffer pH 7+5 mM EDTA until a conductivity of 7 mS/cm was achieved. This solution was applied to a Q-Sepharose FF (diameter 5 cm, length 10 cm) Anion Exchange column, after which the column was washed with 25 mM phosphate buffer pH 7+5 mM EDTA until an absorbency of 0.2 AU. A gradient of 0 to 0.5 M NaCl in 25 mM phosphate pH 7 was applied to the column in 80 minutes followed by a gradient from 0.5 to 1 M NaCl in 10 minutes. Elution took place in the first gradient. After elution the column was cleaned (upflow) with 1 M NaOH and equilibrated again with 25 mM phosphate pH 7+5 mM EDTA. Depending on the elution profile, the obtained cellulase had a purity of up to about 80%.

EXAMPLE 4

Properties of Cellulase According to the Invention

To determine the pH/temperature profile of the approximately 50 kD cellulase according to the invention, the activity of the cellulase was measured on CMC at various pH and temperature values. A solution comprising the approximately 50 kD cellulase was combined in a buffer in diluted with 10 mM phosphate buffer (pH 7). (pH was controlled by using buffer comprising a mixture of 100 ml 1 M phosphoric acid, 100 ml citric acid and 600 ml distilled water having the pH adjusted to 4, 5, 6, 7, 8, 9 or 10 using 4 M NaOH, after which the mixture is filled to 1 L using distilled water). The enzyme solution was diluted until 0.05 U/ml measured at pH 7 and 40° C. Each buffer system was tested to ascertain the actual pH after mixing 0.5 ml Buffer, 0.5 ml substrate (1% CMC) and 0.1 ml 10 mM phosphate buffer. Actual pH for the pH 4, 5, 6, 7, 8, 9 and 10 solutions was 4.2, 5.2, 6.2, 7, 8, 8.7 and 9.9, respectively.

The results are illustrated in FIG. 1 showing the excellent alkaline activity of the cellulase. The slope of the calibration curve is dependent on the pH of the enzyme substrate mixture for that reason two glucose standards at each pH are taken (500 mg glucose. H2)/100 ml 10 and 25 times diluted.

Cellulase activity may be assayed using a modified PAH-BAH method (Lever M. Anal. Biochem. 1972, 47, 273–279 and Lever M. Anal. Biochem. 1977, 81, 21–27) as follows. The pH/temperature profiles may be determined using a fixed enzyme concentration which fits in the linear range of the dose response profile measured at pH 7 and 40° C. This enzyme concentration may be used for the measurement of the activities under all other determined conditions. A test tube is filled with 250 μl 2.5% CMC in 50 mM glycine buffer pH 9 (CMC-low viscosity is purchased from Sigma) and 250 μl aliquots of the 50 kD cellulase, diluted in the appropriate buffer. The test tube is incubated for 30 minutes at 40° C. in a waterbath, whereafter 1.5 ml of a daily fresh prepared PAHBAH solution (1% PAHBAH in 100 ml 0.5 M NaOH with 100 ml bismuth solution (containing 48.5 g bismuth nitrate, 28.2 g potassium sodium tartrate and 12.0 g NaOH in 100 ml) is added. The mixture is heated at 70° C. for 10 minutes, after which it is cooled on ice for 2 minutes. The absorption is measured at 410 nm. To eliminate the background absorbance of the enzyme samples a control experiment is executed as follows: a tube with substrate is incubated under the same conditions as the test tube. After the incubation 1.5 ml PAHBAH and the enzyme preparation is added (in this order). One unit (U) is defined as the amount of enzyme producing 1 μmol of glucose from CMC equivalent determined as reducing sugars per minute per gram product.

I claim:

1. An isolated and purified cellulase obtainable from or derived from Bacillus sp. CBS 670.93, having an amino acid sequence comprising SEQ ID NO:2.

2. A composition comprising a cellulase which comprises an amino acid sequence according to SEQ ID NO:2.

3. The composition according to claim 2, wherein said cellulase is obtained from Bacillus sp. CBS 670.93.

4. A method of treating textiles comprising contacting said textile with the cellulase of claims 1 or 2.

5. A cellulase obtainable from Bacillus sp. CBS 670.93 having an amino acid sequence comprising SEQ ID NO:2, wherein said cellulase is produced by a method comprising the following steps:

(a) transforming a suitable microorganism with DNA encoding said cellulase;

(b) preparing a fermentation broth containing said suitable microorganism under conditions suitable for expression of said DNA;

(c) maintaining said fermentation broth for a time and under conditions to permit the expression of a desired amount of said cellulase; and (d) collecting said fermentation broth which contains said cellulase.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1404 base pairs
        ( B ) TYPE: nucleic acid
        ( C ) STRANDEDNESS: double (D) TOPOLOGY: linear (ii) MOLECULE TYPE: DNA (genomic)

(iii) HYPOTHETICAL: NO (iii) ANTI-SENSE: NO (vi) ORIGINAL SOURCE:
    (A) ORGANISM: Bacillus sp.
    (C) INDIVIDUAL ISOLATE: CBS 670.93

(ix) FEATURE:
    (A) NAME/KEY: sig_peptide
    (B) LOCATION: 1..78

(ix) FEATURE:
    (A) NAME/KEY: mat_peptide
    (B) LOCATION: 79..1404
    (D) OTHER INFORMATION: /function= "endoglucanase"
        / EC_number= 3.2.1.4
        / product= "BCE103 cellulase"

(ix) FEATURE:
    (A) NAME/KEY: CDS
    (B) LOCATION: 1..1404

(xi) SEQUENCE DESCRIPTION: SEQ ID NO: 1:

```
ATG AAA AAG ATA ACT ACT ATT TTT GCC GTA TTG CTC ATG ACA TTG GCG         48
Met Lys Lys Ile Thr Thr Ile Phe Ala Val Leu Leu Met Thr Leu Ala
-26 -25              -20                      -15

TTG TTC AGT ATA GGA AAC ACG ACA GCG GCT GAT GAT TAT TCA GTT GTA         96
Leu Phe Ser Ile Gly Asn Thr Thr Ala Ala Asp Asp Tyr Ser Val Val
-10              -5                   1                    5

GAG GAA CAT GGG CAA CTA AGT ATT AGT AAC GGT GAA TTA GTC AAT GAA        144
Glu Glu His Gly Gln Leu Ser Ile Ser Asn Gly Glu Leu Val Asn Glu
             10              15                      20

CGA GGC GAA CAA GTT CAG TTA AAA GGG ATG AGT TCC CAT GGT TTG CAA        192
Arg Gly Glu Gln Val Gln Leu Lys Gly Met Ser Ser His Gly Leu Gln
         25              30                  35

TGG TAC GGT CAA TTT GTA AAC TAT GAA AGC ATG AAA TGG CTA AGA GAT        240
Trp Tyr Gly Gln Phe Val Asn Tyr Glu Ser Met Lys Trp Leu Arg Asp
     40              45                  50

GAT TGG GGA ATA ACT GTA TTC CGA GCA GCA ATG TAT ACC TCT TCA GGA        288
Asp Trp Gly Ile Thr Val Phe Arg Ala Ala Met Tyr Thr Ser Ser Gly
 55              60                  65                      70

GGA TAT ATT GAC GAT CCA TCA GTA AAG GAA AAA GTA AAA GAG ACT GTT        336
Gly Tyr Ile Asp Asp Pro Ser Val Lys Glu Lys Val Lys Glu Thr Val
                     75              80                  85

GAG GCT GCG ATA GAC CTT GGC ATA TAT GTG ATC ATT GAT TGG CAT ATC        384
Glu Ala Ala Ile Asp Leu Gly Ile Tyr Val Ile Ile Asp Trp His Ile
             90              95                      100

CTT TCA GAC AAT GAC CCG AAT ATA TAT AAA GAA GAA GCG AAG GAT TTC        432
Leu Ser Asp Asn Asp Pro Asn Ile Tyr Lys Glu Glu Ala Lys Asp Phe
         105                 110                 115

TTT GAT GAA ATG TCA GAG TTG TAT GGA GAC TAT CCG AAT GTG ATA TAC        480
Phe Asp Glu Met Ser Glu Leu Tyr Gly Asp Tyr Pro Asn Val Ile Tyr
     120                 125                 130

GAA ATT GCA AAT GAA CCG AAT GGT AGT GAT GTT ACG TGG GAC AAT CAA        528
Glu Ile Ala Asn Glu Pro Asn Gly Ser Asp Val Thr Trp Asp Asn Gln
 135                 140                 145                 150

ATA AAA CCG TAT GCA GAA GAA GTG ATT CCG GTT ATT CGT GAC AAT GAC        576
Ile Lys Pro Tyr Ala Glu Glu Val Ile Pro Val Ile Arg Asp Asn Asp
                 155                 160                 165

CCT AAT AAC ATT GTT ATT GTA GGT ACA GGT ACA TGG AGT CAG GAT GTC        624
Pro Asn Asn Ile Val Ile Val Gly Thr Gly Thr Trp Ser Gln Asp Val
             170                 175                 180
```

| | | | | | | | | | | | | | | | | |
|---|---|---|---|---|---|---|---|---|---|---|---|---|---|---|---|---|
| CAT | CAT | GCA | GCC | GAT | AAT | CAG | CTT | GCA | GAT | CCT | AAC | GTC | ATG | TAT | GCA | 672 |
| His | His | Ala | Ala | Asp | Asn | Gln | Leu | Ala | Asp | Pro | Asn | Val | Met | Tyr | Ala | |
| | 185 | | | | | 190 | | | | | | 195 | | | | |
| TTT | CAT | TTT | TAT | GCA | GGA | ACA | CAT | GGA | CAA | AAT | TTA | CGA | GAC | CAA | GTA | 720 |
| Phe | His | Phe | Tyr | Ala | Gly | Thr | His | Gly | Gln | Asn | Leu | Arg | Asp | Gln | Val | |
| | 200 | | | | | 205 | | | | | | 210 | | | | |
| GAT | TAT | GCA | TTA | GAT | CAA | GGA | GCA | GCG | ATA | TTT | GTT | AGT | GAA | TGG | GGG | 768 |
| Asp | Tyr | Ala | Leu | Asp | Gln | Gly | Ala | Ala | Ile | Phe | Val | Ser | Glu | Trp | Gly | |
| 215 | | | | | 220 | | | | | 225 | | | | | 230 | |
| ACA | AGT | GCA | GCT | ACA | GGT | GAT | GGT | GGT | GTG | TTT | TTA | GAT | GAA | GCA | CAA | 816 |
| Thr | Ser | Ala | Ala | Thr | Gly | Asp | Gly | Gly | Val | Phe | Leu | Asp | Glu | Ala | Gln | |
| | | | | 235 | | | | | 240 | | | | | 245 | | |
| GTG | TGG | ATT | GAC | TTT | ATG | GAT | GAA | AGA | AAT | TTA | AGC | TGG | GCC | AAC | TGG | 864 |
| Val | Trp | Ile | Asp | Phe | Met | Asp | Glu | Arg | Asn | Leu | Ser | Trp | Ala | Asn | Trp | |
| | | | 250 | | | | | 255 | | | | | 260 | | | |
| TCT | CTA | ACG | CAT | AAG | GAT | GAG | TCA | TCT | GCA | GCG | TTA | ATG | CCA | GGT | GCA | 912 |
| Ser | Leu | Thr | His | Lys | Asp | Glu | Ser | Ser | Ala | Ala | Leu | Met | Pro | Gly | Ala | |
| | | 265 | | | | | 270 | | | | | 275 | | | | |
| AAT | CCA | ACT | GGT | GGT | TGG | ACA | GAG | GCT | GAA | CTA | TCT | CCA | TCT | GGT | ACA | 960 |
| Asn | Pro | Thr | Gly | Gly | Trp | Thr | Glu | Ala | Glu | Leu | Ser | Pro | Ser | Gly | Thr | |
| | 280 | | | | | 285 | | | | | | 290 | | | | |
| TTT | GTG | AGG | GAA | AAA | ATA | AGA | GAA | TCA | GCA | TCT | ATT | CCG | CCA | AGC | GAT | 1008 |
| Phe | Val | Arg | Glu | Lys | Ile | Arg | Glu | Ser | Ala | Ser | Ile | Pro | Pro | Ser | Asp | |
| 295 | | | | | 300 | | | | | 305 | | | | | 310 | |
| CCA | ACA | CCG | CCA | TCT | GAT | CCA | GGA | GAA | CCG | GAT | CCA | GGA | GAA | CCG | GAT | 1056 |
| Pro | Thr | Pro | Pro | Ser | Asp | Pro | Gly | Glu | Pro | Asp | Pro | Gly | Glu | Pro | Asp | |
| | | | | 315 | | | | | 320 | | | | | 325 | | |
| CCA | ACG | CCC | CCA | AGT | GAT | CCA | GGA | GAG | TAT | CCA | GCA | TGG | GAT | TCA | AAT | 1104 |
| Pro | Thr | Pro | Pro | Ser | Asp | Pro | Gly | Glu | Tyr | Pro | Ala | Trp | Asp | Ser | Asn | |
| | | | 330 | | | | | 335 | | | | | 340 | | | |
| CAA | ATT | TAC | ACA | AAT | GAA | ATT | GTG | TAT | CAT | AAC | GGT | CAG | TTA | TGG | CAA | 1152 |
| Gln | Ile | Tyr | Thr | Asn | Glu | Ile | Val | Tyr | His | Asn | Gly | Gln | Leu | Trp | Gln | |
| | | 345 | | | | | 350 | | | | | 355 | | | | |
| GCG | AAA | TGG | TGG | ACA | CAA | AAT | CAA | GAG | CCA | GGT | GAC | CCA | TAC | GGT | CCG | 1200 |
| Ala | Lys | Trp | Trp | Thr | Gln | Asn | Gln | Glu | Pro | Gly | Asp | Pro | Tyr | Gly | Pro | |
| | 360 | | | | | 365 | | | | | 370 | | | | | |
| TGG | GAA | CCA | CTC | AAA | TCT | GAC | CCA | GAT | TCA | GGA | GAA | CCG | GAT | CCA | ACG | 1248 |
| Trp | Glu | Pro | Leu | Lys | Ser | Asp | Pro | Asp | Ser | Gly | Glu | Pro | Asp | Pro | Thr | |
| 375 | | | | | 380 | | | | | 385 | | | | | 390 | |
| CCC | CCA | AGT | GAT | CCA | GGA | GAG | TAT | CCA | GCA | TGG | GAT | TCA | AAT | CAA | ATT | 1296 |
| Pro | Pro | Ser | Asp | Pro | Gly | Glu | Tyr | Pro | Ala | Trp | Asp | Ser | Asn | Gln | Ile | |
| | | | | 395 | | | | | 400 | | | | | 405 | | |
| TAC | ACA | AAT | GAA | ATT | GTG | TAC | CAT | AAC | GGC | CAG | CTA | TGG | CAA | GCA | AAA | 1344 |
| Tyr | Thr | Asn | Glu | Ile | Val | Tyr | His | Asn | Gly | Gln | Leu | Trp | Gln | Ala | Lys | |
| | | | 410 | | | | | 415 | | | | | 420 | | | |
| TGG | TGG | ACA | CAA | AAT | CAA | GAG | CCA | GGT | GAC | CCA | TAT | GGT | CCG | TGG | GAA | 1392 |
| Trp | Trp | Thr | Gln | Asn | Gln | Glu | Pro | Gly | Asp | Pro | Tyr | Gly | Pro | Trp | Glu | |
| | | 425 | | | | | 430 | | | | | 435 | | | | |
| CCA | CTC | AAT | TAA | | | | | | | | | | | | | 1404 |
| Pro | Leu | Asn | | | | | | | | | | | | | | |
| | | 440 | | | | | | | | | | | | | | |

( 2 ) INFORMATION FOR SEQ ID NO: 2:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Lys  Lys  Ile  Thr  Thr  Ile  Phe  Ala  Val  Leu  Leu  Met  Thr  Leu  Ala
-26  -25                 -20                      -15

Leu  Phe  Ser  Ile  Gly  Asn  Thr  Thr  Ala  Ala  Asp  Asp  Tyr  Ser  Val  Val
-10                      -5                    1                      5

Glu  Glu  His  Gly  Gln  Leu  Ser  Ile  Ser  Asn  Gly  Glu  Leu  Val  Asn  Glu
              10                      15                      20

Arg  Gly  Glu  Gln  Val  Gln  Leu  Lys  Gly  Met  Ser  Ser  His  Gly  Leu  Gln
              25                      30                      35

Trp  Tyr  Gly  Gln  Phe  Val  Asn  Tyr  Glu  Ser  Met  Lys  Trp  Leu  Arg  Asp
     40                      45                      50

Asp  Trp  Gly  Ile  Thr  Val  Phe  Arg  Ala  Ala  Met  Tyr  Thr  Ser  Ser  Gly
55                       60                      65                           70

Gly  Tyr  Ile  Asp  Asp  Pro  Ser  Val  Lys  Glu  Lys  Val  Lys  Glu  Thr  Val
                   75                      80                           85

Glu  Ala  Ala  Ile  Asp  Leu  Gly  Ile  Tyr  Val  Ile  Ile  Asp  Trp  His  Ile
              90                      95                           100

Leu  Ser  Asp  Asn  Asp  Pro  Asn  Ile  Tyr  Lys  Glu  Glu  Ala  Lys  Asp  Phe
          105                      110                      115

Phe  Asp  Glu  Met  Ser  Glu  Leu  Tyr  Gly  Asp  Tyr  Pro  Asn  Val  Ile  Tyr
     120                      125                      130

Glu  Ile  Ala  Asn  Glu  Pro  Asn  Gly  Ser  Asp  Val  Thr  Trp  Asp  Asn  Gln
135                       140                      145                      150

Ile  Lys  Pro  Tyr  Ala  Glu  Glu  Val  Ile  Pro  Val  Ile  Arg  Asp  Asn  Asp
                    155                      160                      165

Pro  Asn  Asn  Ile  Val  Ile  Val  Gly  Thr  Gly  Thr  Trp  Ser  Gln  Asp  Val
               170                      175                      180

His  His  Ala  Ala  Asp  Asn  Gln  Leu  Ala  Asp  Pro  Asn  Val  Met  Tyr  Ala
          185                      190                      195

Phe  His  Phe  Tyr  Ala  Gly  Thr  His  Gly  Gln  Asn  Leu  Arg  Asp  Gln  Val
     200                      205                      210

Asp  Tyr  Ala  Leu  Asp  Gln  Gly  Ala  Ala  Ile  Phe  Val  Ser  Glu  Trp  Gly
215                       220                      225                      230

Thr  Ser  Ala  Ala  Thr  Gly  Asp  Gly  Gly  Val  Phe  Leu  Asp  Glu  Ala  Gln
                    235                      240                      245

Val  Trp  Ile  Asp  Phe  Met  Asp  Glu  Arg  Asn  Leu  Ser  Trp  Ala  Asn  Trp
               250                      255                      260

Ser  Leu  Thr  His  Lys  Asp  Glu  Ser  Ser  Ala  Ala  Leu  Met  Pro  Gly  Ala
          265                      270                      275

Asn  Pro  Thr  Gly  Gly  Trp  Thr  Glu  Ala  Glu  Leu  Ser  Pro  Ser  Gly  Thr
     280                      285                      290

Phe  Val  Arg  Glu  Lys  Ile  Arg  Glu  Ser  Ala  Ser  Ile  Pro  Pro  Ser  Asp
295                       300                      305                      310

Pro  Thr  Pro  Pro  Ser  Asp  Pro  Gly  Glu  Pro  Asp  Pro  Gly  Glu  Pro  Asp
                    315                      320                      325

Pro  Thr  Pro  Pro  Ser  Asp  Pro  Gly  Glu  Tyr  Pro  Ala  Trp  Asp  Ser  Asn
                    330                      335                      340

Gln  Ile  Tyr  Thr  Asn  Glu  Ile  Val  Tyr  His  Asn  Gly  Gln  Leu  Trp  Gln
          345                      350                      355

Ala  Lys  Trp  Trp  Thr  Gln  Asn  Gln  Glu  Pro  Gly  Asp  Pro  Tyr  Gly  Pro
     360                      365                      370

Trp  Glu  Pro  Leu  Lys  Ser  Asp  Pro  Asp  Ser  Gly  Glu  Pro  Asp  Pro  Thr
375                       380                      385                      390

Pro  Pro  Ser  Asp  Pro  Gly  Glu  Tyr  Pro  Ala  Trp  Asp  Ser  Asn  Gln  Ile
```

-continued

```
                        395                           400                           405
Tyr  Thr  Asn  Glu  Ile  Val  Tyr  His  Asn  Gly  Gln  Leu  Trp  Gln  Ala  Lys
               410                      415                      420

Trp  Trp  Thr  Gln  Asn  Gln  Glu  Pro  Gly  Asp  Pro  Tyr  Gly  Pro  Trp  Glu
               425                 430                      435

Pro  Leu  Asn
          440
```